United States Patent
Kapadia

(10) Patent No.: US 12,226,177 B2
(45) Date of Patent: Feb. 18, 2025

(54) SURGICAL ROBOTIC SYSTEMS

(71) Applicant: Covidien LP, Mansfield, MA (US)

(72) Inventor: Jaimeen Kapadia, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 1083 days.

(21) Appl. No.: 17/257,374

(22) PCT Filed: Jun. 25, 2019

(86) PCT No.: PCT/US2019/038871
§ 371 (c)(1),
(2) Date: Dec. 31, 2020

(87) PCT Pub. No.: WO2020/009831
PCT Pub. Date: Jan. 9, 2020

(65) Prior Publication Data
US 2021/0169593 A1     Jun. 10, 2021

Related U.S. Application Data

(60) Provisional application No. 62/693,488, filed on Jul. 3, 2018.

(51) Int. Cl.
*A61B 34/35* (2016.01)
*A61B 34/30* (2016.01)
*B25J 9/10* (2006.01)

(52) U.S. Cl.
CPC ............ *A61B 34/35* (2016.02); *B25J 9/1035* (2013.01); *A61B 2034/302* (2016.02)

(58) Field of Classification Search
None
See application file for complete search history.

(56) References Cited

U.S. PATENT DOCUMENTS

2011/0040150 A1    2/2011  Govari et al.
2013/0123783 A1*   5/2013  Marczyk ............ A61B 18/1445
                                                   606/1
(Continued)

FOREIGN PATENT DOCUMENTS

CN      103110456 A      5/2013
DE    102010006617 A1 *  8/2011  .............. B25J 9/102
(Continued)

OTHER PUBLICATIONS

Supplementary European Search Report dated Mar. 17, 2022, issued in corresponding EP Appln. No. 19831523, 30 pages.
(Continued)

*Primary Examiner* — Martin T Ton
(74) *Attorney, Agent, or Firm* — Carter, DeLuca & Farrell LLP

(57) ABSTRACT

An instrument drive unit for use in a robotic surgical system includes a carriage configured to be coupled to a robotic arm, a hub rotationally coupled to the carriage and configured to be non-rotatably coupled to an electromechanical surgical instrument, a plurality of motors, a plurality of motor gears, a plurality of drive shafts, and a plurality of drive gears. Each motor gear is operably coupled to a corresponding motor, and each drive gear is fixed to a corresponding drive shaft. The drive shafts are rotationally supported in the hub and configured for interfacing with a corresponding driven member of the electromechanical surgical instrument. Each motor gear is configured to rotate a corresponding drive gear in response to an activation of a respective motor to actuate a function of the electromechanical surgical instrument.

18 Claims, 7 Drawing Sheets

(56) References Cited

U.S. PATENT DOCUMENTS

| | | | |
|---|---|---|---|
| 2013/0296886 A1 | 11/2013 | Green et al. | |
| 2016/0066982 A1 | 3/2016 | Marczyk et al. | |
| 2017/0020617 A1 | 1/2017 | Weir et al. | |
| 2017/0367782 A1 | 12/2017 | Schuh et al. | |
| 2018/0049835 A1 | 2/2018 | Shelton, IV et al. | |
| 2019/0208989 A1* | 7/2019 | Xu .................. | A61B 17/00234 |
| 2021/0015572 A1* | 1/2021 | Gomez ................ | A61B 34/35 |

FOREIGN PATENT DOCUMENTS

| | | |
|---|---|---|
| KR | 101778031 B1 | 9/2017 |
| WO | 2017205311 A1 | 11/2017 |
| WO | 2018041218 A1 | 3/2018 |
| WO | 2018085529 A2 | 5/2018 |

OTHER PUBLICATIONS

Office Action Dated Jul. 21, 2023 for Chinese Patent Application No. 201980055422X (19 pages).
International Search Report dated Oct. 14, 2019, issued in corresponding international application PCT/US2019/038871, 3 pages.
Written Opinion of the International Searching Authority dated Oct. 14, 2019, issued in corresponding international application PCT/US2019/038871, 5 pages.

* cited by examiner

SURGICAL ROBOTIC SYSTEMS

CROSS-REFERENCE TO RELATED APPLICATIONS

This application is a National Stage Application of PCT Application No. PCT/US2019/038871 under 35 USC § 371(a), filed Jun. 25, 2019, which claims the benefit of and priority to U.S. Provisional Application No. 62/693,488, filed Jul. 3, 2018. Each of these disclosures are hereby incorporated by reference herein.

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument.

SUMMARY

In accordance with an aspect of the present disclosure, an instrument drive unit for use in a robotic surgical system is provided and includes a carriage configured to be coupled to a robotic arm, a hub rotationally coupled to the carriage and configured to be non-rotatably coupled to an electromechanical surgical instrument, a plurality of motors, a plurality of motor gears, a plurality of drive shafts, and a plurality of drive gears. Each motor gear is operably coupled to a corresponding motor, and each drive gear is fixed to a corresponding drive shafts. The drive shafts are rotationally supported in the hub and configured for interfacing with a corresponding driven member of the electromechanical surgical instrument. Each motor gear is configured to rotate a corresponding drive gear in response to an activation of a respective motor to actuate a function of the electromechanical surgical instrument.

In aspects, the instrument drive unit may further include a drive motor operably coupled to the hub and configured to rotate the hub about a central longitudinal axis defined by the hub.

In other aspects, the drive motor may have a rotatable coupling fixed to the hub to transfer torque from the drive motor to the hub.

In further aspects, the motors may be circumferentially spaced from one another and disposed about the hub and the drive motor.

The instrument drive unit may further include a sleeve rotatably coupled to a distal end portion of the carriage and non-rotatably coupled to the hub. The sleeve may be configured to non-rotatably receive the electromechanical surgical instrument, such that a rotation of the hub results in a rotation of the electromechanical surgical instrument.

In aspects, the instrument drive unit may further include a plurality of ring gears operably coupling a corresponding motor gear with a corresponding drive gear.

In other aspects, the ring gears may be vertically stacked within the hub.

In further aspects, a first ring gear and a first drive gear may be operably coupled to one another and aligned along a first horizontal plane, and a second ring gear and a second drive gear may be operably coupled to one another and aligned along a second horizontal plane, vertically displaced from the first horizontal plane.

The ring gears may be independently rotatable relative to one another.

In aspects, a first ring gear may have gear teeth on an inner periphery thereof and an outer periphery thereof. The gear teeth on the inner periphery may interface with a corresponding drive gear, and the gear teeth on the outer periphery may interface with a corresponding motor gear.

In other aspects, the drive shafts may be circumferentially spaced from one another about the hub.

In further aspects, the drive gears may be vertically offset from one another.

The motor gears may be vertically offset from one another.

In aspects, the instrument drive unit may further include a plurality of motor shafts extending distally from a corresponding motor. Each motor gear may be fixed to a corresponding motor shaft.

In other aspects, each drive shaft may have a distal end portion configured for interfacing with a corresponding driven member of the electromechanical surgical instrument.

In another aspect of the present disclosure, an instrument drive unit for use in a robotic surgical system is provided and includes a carriage configured to be coupled to a robotic arm, a plurality of motors supported in the carriage, a plurality of motor shafts, and a plurality of drive shafts circumferentially spaced from one another and configured for interfacing with a corresponding driven member of an electromechanical surgical instrument. Each motor shaft extends distally from a corresponding motor, and each motor shaft has a motor gear fixed thereabout. Each drive shaft has a drive gear fixed thereabout, and each drive gear is disposed at a discrete vertical location relative to one another. Each motor gear is configured to rotate a corresponding drive gear in response to an activation of a respective motor to actuate a function of the electromechanical surgical instrument.

In aspects, the instrument drive unit may further include a plurality of vertically stacked ring gears operably coupling a corresponding motor gear with a corresponding drive gear, such that each motor gear is configured to rotate a corresponding drive gear in response to an activation of a respective motor to actuate a function of the electromechanical surgical instrument.

In other aspects, the instrument drive unit may further include a hub rotationally coupled to the carriage, and a drive motor operably coupled to the hub. The hub may be configured to be non-rotatably coupled to the electromechanical surgical instrument. The drive shafts may be rotationally supported in the hub. The drive motor may be configured to rotate the hub about a central longitudinal axis defined by the hub.

In further aspects, the instrument drive unit may further include a sleeve rotatably coupled to a distal end portion of the carriage and non-rotatably coupled to the hub. The sleeve may be configured to non-rotatably receive the electromechanical surgical instrument, such that a rotation of the hub results in a rotation of the electromechanical surgical instrument.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
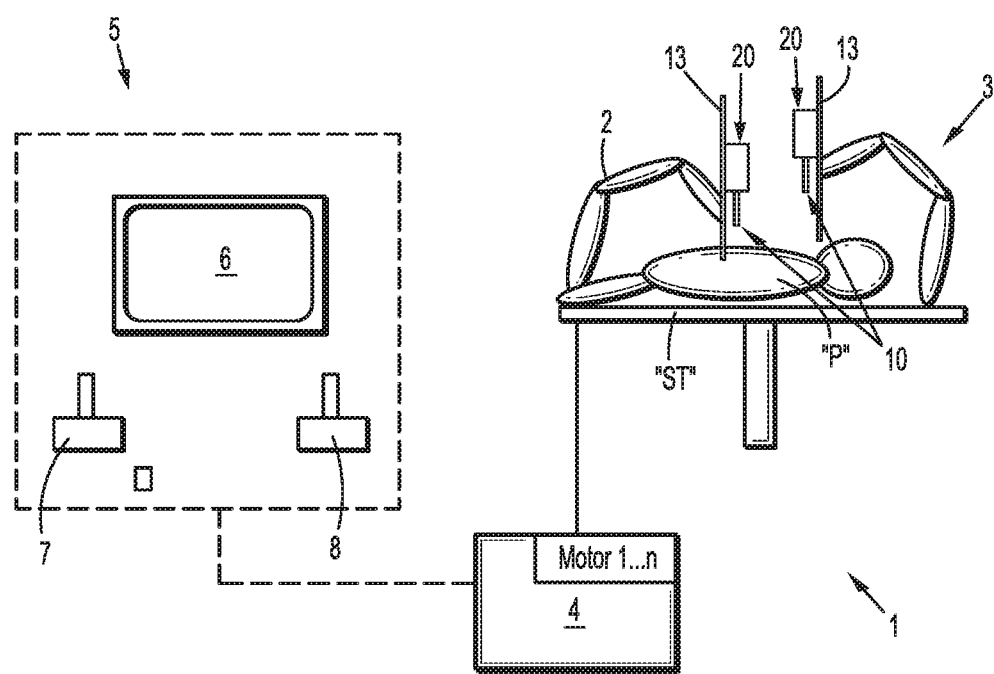
FIG. 1 is a schematic illustration of a surgical robotic system including an instrument drive unit coupled to a slide in accordance with the present disclosure.

Embodiments of the presently disclosed surgical robotic system and instrument drive units thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient.

As will be described in detail below, provided is an instrument drive unit of a surgical robotic system configured to allow for a bottom-loading of a surgical instrument. The instrument drive unit has a plurality of drive shafts each configured to be coupled to a corresponding driven member of the surgical instrument for carrying out a discrete function of the surgical instrument. The drive shafts of the instrument drive unit are operably coupled to a discrete motor of the instrument drive unit via a discrete transmission assembly. The configuration of the transmission assemblies allows for a reduction in the overall height of the instrument drive unit (e.g., the instrument drive unit is more compact). For example, gears of the transmission assemblies are vertically and horizontally offset from the gears of the other transmission assemblies. The instrument drive unit may also include a rotatable hub that rotationally supports the drive shafts. The hub is configured to be rotated via a separate drive motor to enable rotation of the attached surgical instrument about its longitudinal axis. Other features and benefits of the disclosed instrument drive units are further detailed below.

Referring initially to FIG. 1, a surgical system, such as, for example, a surgical robotic system 1, generally includes a plurality of surgical robotic arms 2, 3; an elongated slide 13 coupled to an end of each of the robotic arms 2, 3; an instrument drive unit 20 and an electromechanical instrument 10 removably attached to the slide 13 and configured to move along the slide 13; a control device 4; and an operating console 5 coupled with control device 4. The operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of the instrument drive unit 20 along the slide 13, movement of the robotic arms 2, 3, and/or movement of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 (including an electromechanical end effector), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of drive motors 22 (FIGS. 2 and 3) of the instrument drive unit 20 to drive various operations of the surgical instrument 10. The instrument drive unit 20 transfers power and actuation forces from its motors to driven members (not shown) of the electromechanical instrument 10 to ultimately drive movement of components of the end effector of the electromechanical instrument 10, for example, a movement of a knife blade (not shown) and/or a closing and opening of jaw members of the end effector.

For a detailed description of the construction and operation of a robotic surgical system, reference may be made to U.S. Pat. No. 8,828,023, entitled "Medical Workstation," the entire contents of which are incorporated by reference herein.

With reference to FIGS. 2-7, the instrument drive unit 20 will now be described in detail. The instrument drive unit 20 includes a carriage 26 and a coupling or sleeve 28 rotatably coupled to a distal end portion 26b of the carriage 26 for connecting a surgical instrument 10 (FIG. 1) to the instrument drive unit 20. The carriage 26 of the instrument drive unit 20 is configured to be slidably coupled to a linear track (not shown) defined longitudinally along the slide 13 (FIG. 1). A proximal end portion 26a of the carriage 26 houses a plurality of drive motors 22a, 22b, 22c, 22d, 22d, 22e (collectively referred herein as "22") for carrying out various functions of an attached surgical instrument. The distal end portion 26b of the carriage 26 defines a longitudinally-extending channel 30 therethrough dimensioned for receipt of a hub 46 of the instrument drive unit 20. The distal end portion 26b has an annular ledge 32 (FIGS. 5 and 6) that extends radially inward from an inner peripheral surface of the carriage 26. The annular ledge 32 is configured to support internal components of the instrument drive unit 20.

In embodiments, the distal end portion 26b of the carriage 26 may have a slip ring 33 received therein for transferring electrical signals or power between fixed structures (e.g., the drive motors 22) and rotating structures (e.g., the electromechanical surgical instrument 10). The electrical signals transferred by the slip ring 33 may be feedback signals from the electromechanical surgical instrument 10 relating to the status and location of the surgical instrument 10 and/or the status and location of adjacent tissue structures. For example, the feedback may include the temperature of the surgical instrument 10, forces experienced by the surgical instrument 10, and/or the position of certain structures of the surgical instrument 10 relative to one another or relative to the adjacent tissue structures.

Figure 2:
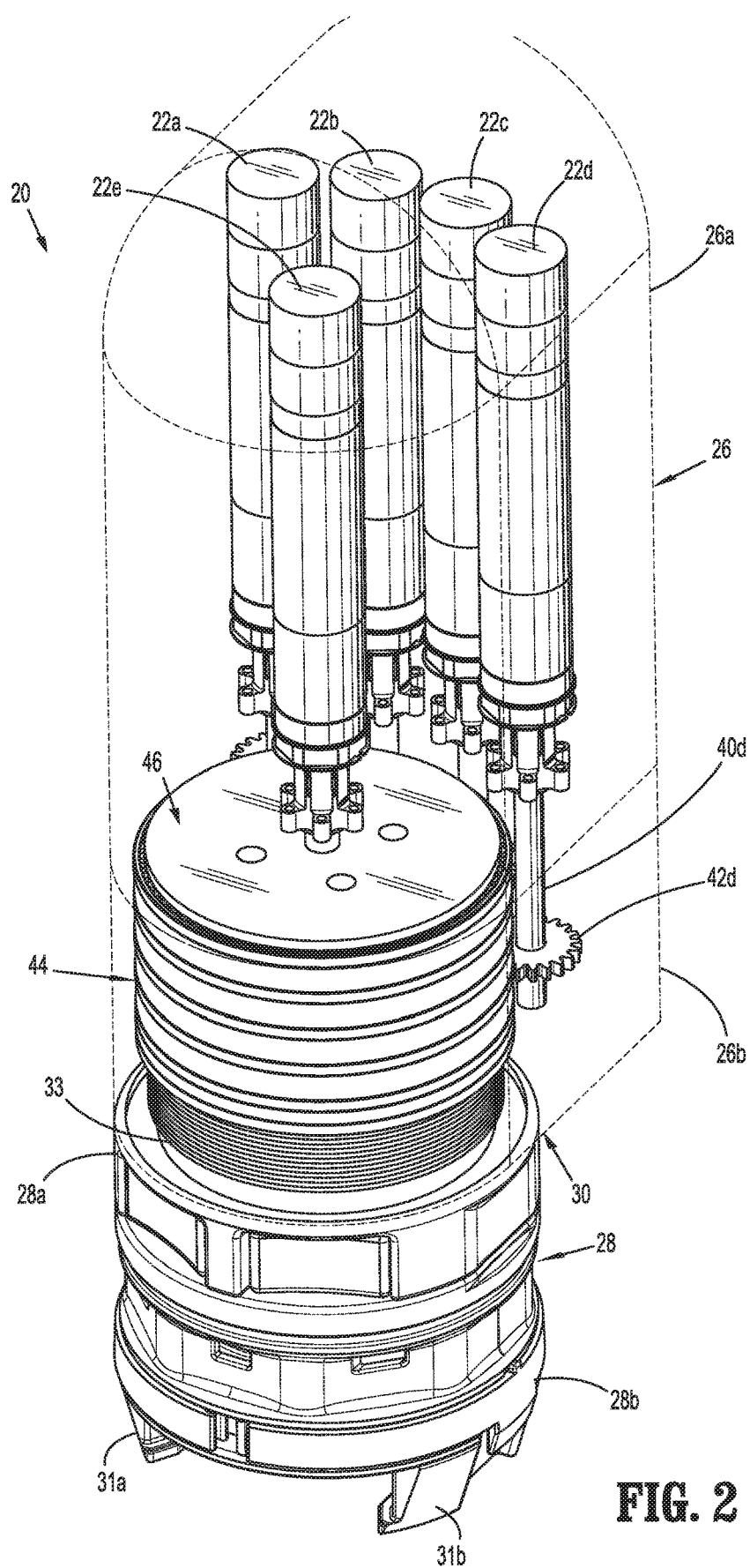
FIG. 2 is a perspective view of the instrument drive unit of the surgical robotic system of FIG. 1.

With reference to FIG. 2, the coupling or sleeve 28 of the instrument drive unit 20 is rotatably coupled to the distal end portion 26b of the carriage 26. The sleeve 28 has a proximal end portion 28a received within the channel 30 of the carriage 26 and fixed to the hub 46, such that the sleeve 28 rotates with the hub 46. The sleeve 28 has a plurality of annular members 29 (FIG. 5) fixed therein having a respective drive shaft 66 extending therethrough. Rotation of the hub 46 causes the drive shafts 66 to rotate therewith, which, in turn, drives a rotation of the sleeve 28, as will be described. The sleeve 28 has a distal end portion 28b configured to non-rotationally fix the main body portion of the surgical instrument 10 therein. The sleeve 28 may have a pair of latch members 31a, 31b configured to releasably retain the main body portion of the electromechanical surgical instrument 10. Accordingly, when the surgical instrument 10 is coupled to the instrument drive unit 20, a rotation of the sleeve 28 results in a rotation of the attached surgical instrument 28.

Figure 3:
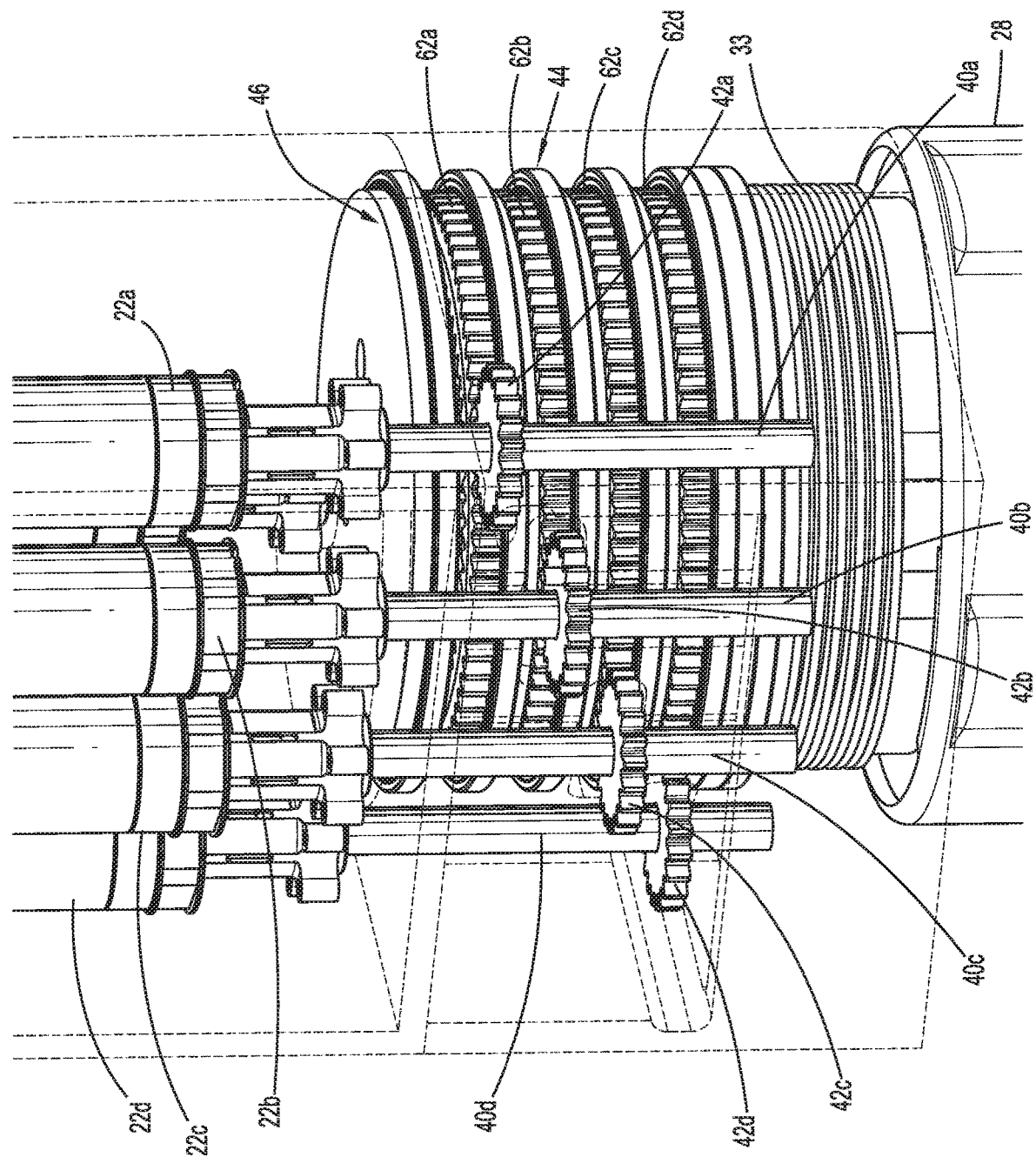
FIG. 3 is an enlarged, rear perspective view of the instrument drive unit of FIG. 2.

With reference to FIGS. 2 and 3, the motors 22 of the instrument drive unit 20 are concealed within the proximal end portion 26a of the carriage 26. The drive motors 22a, 22b, 22c, 22d are circumferentially spaced from one another and are independently actuatable via the control device 4 (FIG. 1). One of the drive motors, such as, for example, drive motor 22e, is configured to effectuate a rotation of the surgical instrument 10 when the surgical instrument 10 is coupled to the instrument drive unit 20, and the remaining drive motors 22a, 22b, 22c, 22d are configured to actuate functions of the surgical instrument 10. The drive motors 22a, 22b, 22c, 22d are disposed about the fifth drive motor 22e. The drive motors 22 may be cylindrical or pancake motors. Other types of motors are also contemplated.

While the instrument drive unit 20 is illustrated as having five drive motors, it is contemplated that the instrument drive unit 20 may have more or less than five drive motors.

The first four drive motors 22a, 22b, 22c, 22d each have a rotatable motor shaft 40a, 40b, 40c, 40d (collectively referred to herein as "40") extending distally therefrom and through the distal end portion 26b of the carriage 26. The motor shafts 40 are circumferentially spaced from one another about the channel 30 of the distal end portion 26b of the carriage 26 and the hub 46. The motor shafts 40 each have a motor gear 42a, 42b, 42c, 42d (collectively referred to herein as "42"), such as, for example, a spur gear, rotationally fixed thereabout. Each of the motor gears 42 are positioned at a discrete vertical location on their respective motor shaft 40, such that the motor gears 42 are vertically offset a selected distance from one another. Since the motor gears 42, in addition to be vertically offset from one another, are also circumferentially spaced from one another, the motor gears 42 are offset from one another in all three dimensions.

Figure 5:
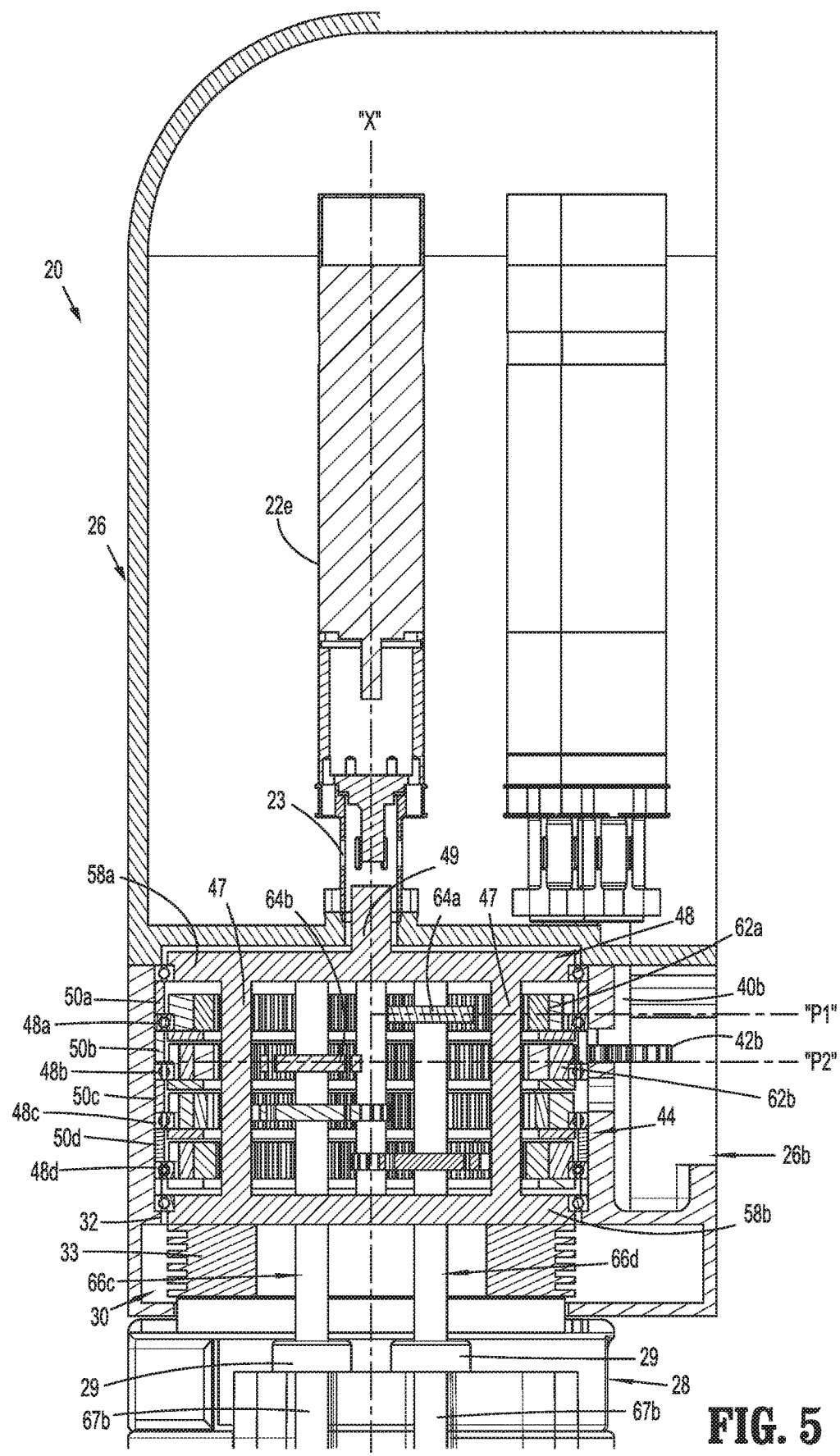
FIG. 5 is a longitudinal cross-sectional view of the instrument drive unit of FIG. 2.
Figure 6:
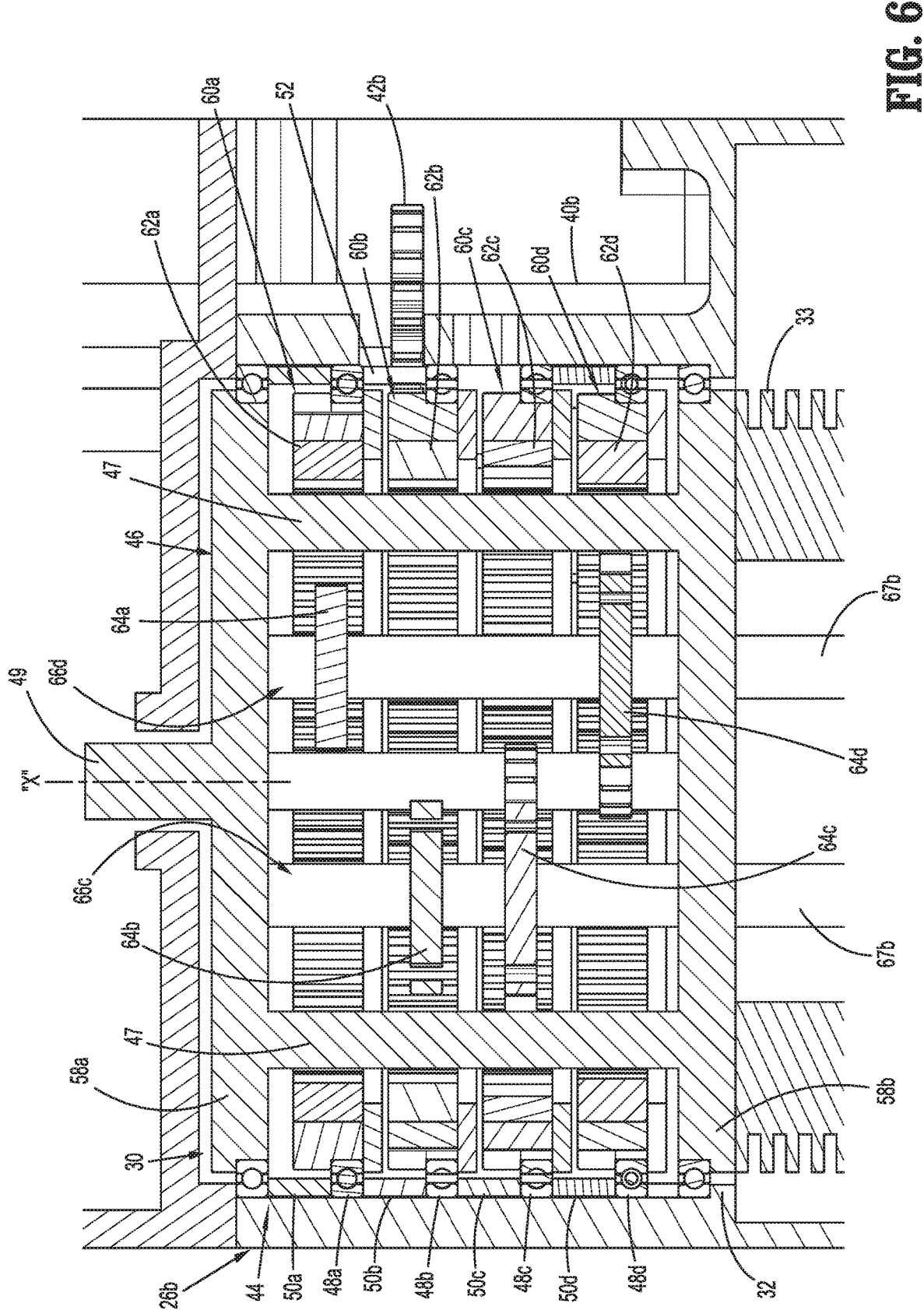
FIG. 6 is an enlarged longitudinal cross-sectional view of the instrument drive unit of FIG. 2.

With reference to FIGS. 2, 3, 5, and 6, the instrument drive unit 20 further includes an outer housing assembly 44 received in the channel 30 of the distal end portion 26b of the carriage 26. The outer housing assembly 44 may be non-rotatably fixed to the distal end portion 26b of the carriage 26 and supported on the ledge 32. As best shown in FIGS. 5 and 6, the outer housing assembly 44 includes a plurality of bearings 48a, 48b, 48c, 48d (collectively referred to herein as "48"), or the like, and a plurality of ring supports 50a, 50b, 50c, 50d (collectively referred to herein as "50") interposed between and fixed with adjacent bearings 48. The ring supports 50 and the bearings 48 are vertically stacked within the channel 30 of the carriage 26 in an alternating arrangement. The ring supports 50 interconnect adjacent bearings 48, such that the entire outer housing assembly 44 is configured as a unitary structure. Each of the ring supports 50 has an opening 52 having a corresponding motor gear 42 extending therethrough to allow the motor gears 42 to interface with a corresponding ring gear 62, as will be described.

Figure 4:
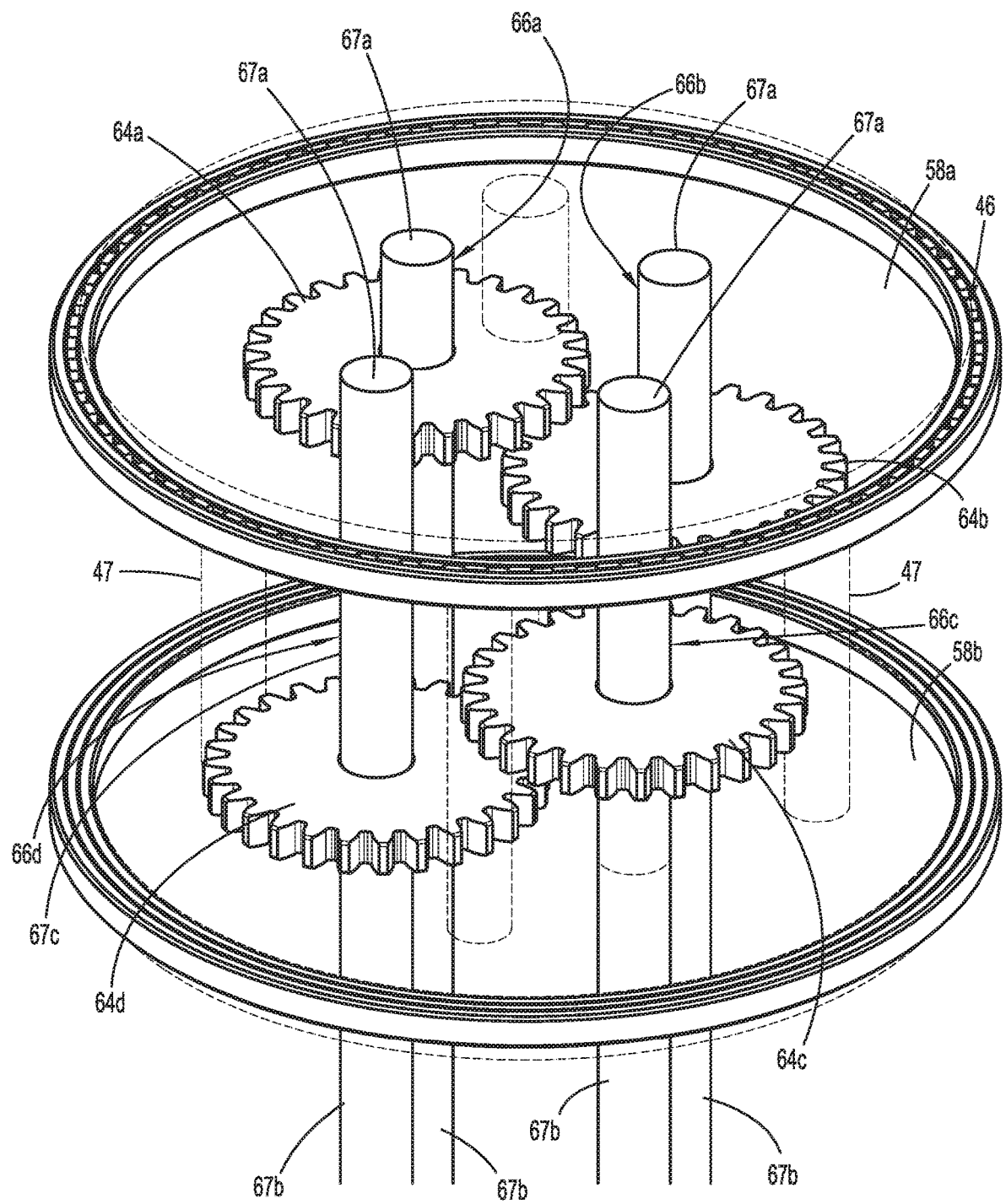
FIG. 4 is a perspective view of a hub of the instrument drive unit of FIG. 2.

With reference to FIGS. 4-6, the hub 46 of the instrument drive unit 20 is supported in the outer housing assembly 44 and is configured to rotate relative to and within the outer housing assembly 44. The hub 46 has a pair of proximal and distal radial extensions 58a, 58b disposed adjacent respective proximal and distal ends thereof. The radial extensions 58a, 58b axially support the hub 46 in the channel 30 of the distal end portion 26b of the carriage 26. The hub 46 has a plurality of support struts 47 extending vertically between the radial extensions 58a, 58b, thereby connecting the radial extensions 58a, 58b and providing integrity to the overall hub 46.

The hub 46 further includes a protuberance 49 extending proximally from a central location of the proximal radial extension 58a. The protuberance 49 of the hub 46 is non-rotatably fixed to a coupling, such as, for example, a sleeve coupling 23, of the fifth drive motor 22e to receive torque from the fifth drive motor 22e. As such, a rotation of the sleeve coupling 23 of the fifth motor 22e drives a rotation of the hub 46 relative to the carriage 26 about a central longitudinal axis "X" defined by the hub 46.

With reference to FIGS. 4-7, the instrument drive unit 20 further includes a plurality of transmission assemblies 60a, 60b, 60c, 60d (collectively referred to herein as "60") that function independently from one another to transfer torque from a corresponding drive motor 22 to a corresponding driven member of the attached surgical instrument 10. Each transmission assembly 60a, 60b, 60c, 60d may include a respective motor gear 42, a ring gear 62a, 62b, 62c, 62d (collectively referred to herein as "62"), a drive gear 64a, 64b, 64c, 64d (collectively referred to herein as "64"), and a drive shaft 66a, 66b, 66c, 66d (collectively referred to herein as "66") operably coupled to one another.

Components of the transmission assemblies 60 are vertically offset from one another along the central longitudinal axis "X" defined by the hub 46, and certain components of each transmission assembly 60 are aligned along a horizontal plane. For example, as best shown in FIGS. 5 and 6, the first motor gear 42a, the first ring gear 62a, and the first drive gear 64a of the first transmission assembly 60a (e.g., the proximal-most transmission assembly) are operably coupled to one another and substantially aligned along a first horizontal plane "P1," and the second motor gear 42b, the second ring gear 62b, and the second drive gear 64b of the second transmission assembly 60b are operably coupled to one another and substantially aligned along a second horizontal plane "P2," which is vertically displaced (e.g., disposed distally) from the first horizontal plane "P1" along the longitudinal axis "X." The remaining transmission assemblies 60c and 60d are also disposed in a discrete horizontal plane. While only four transmission assemblies are shown, it is contemplated that the instrument drive unit 20 may have more or less than four transmission assemblies.

The ring gears 62 of the transmission assemblies 60 are vertically stacked within the hub 46. In particular, the ring gears 62 are coaxial along the central longitudinal axis "X" defined by the hub 46. The ring gears 62 are rotationally supported by a respective bearing 48 of the outer housing assembly 44. The ring gears 62 are disposed about the support struts 47 of the housing 46 and are interposed between the proximal and distal radial extensions 58a, 58b.

Each of the ring gears 62 has gear teeth 68 extending from both an inner periphery 70 thereof and an outer periphery 72 thereof. The gear teeth 68 on the outer periphery 72 of each of the ring gears 62 interfaces with a corresponding motor gear 42, and the gear teeth 68 on the inner periphery 70 of each of the ring gears 62 interfaces with a corresponding drive gear 64, as will be described. In embodiments, each of the rings gears 62 may be constructed from inner and outer ring gears integrally formed with one another.

The drive shafts 66a, 66b, 66c, 66d of the transmission assemblies 60a, 60b, 60c, 60d extend longitudinally through the hub 46 and distally therefrom. In particular, each of the drive shafts 66 has proximal end portions 67a rotatably coupled to the proximal radial extension 58a of the hub 46, intermediate portions 67c extending between the proximal and distal radial extensions 58a, 58b of the hub 46, and distal end portions 67b extending distally from the distal radial extension 58b of the hub 46. The drive shafts 66 are circumferentially spaced from one another about the central longitudinal axis "X" of the hub 46. The drive shafts 66 are free to rotate about their respective longitudinal axes in relation to the hub 46.

The distal end portion 67b of each of the drive shafts 66 is configured to operably couple to a driven member (not explicitly shown) of the surgical instrument 10. For example, the distal end portion 67b of each of the drive shafts 66 may have a coupler (e.g., a gear) for coupling with a corresponding coupler of a driven member of the surgical instrument 10. Accordingly, upon bottom-loading of the electromechanical instrument 10 into the instrument drive unit 20, the distal end portions 67b of the drive shafts 66 of the instrument drive unit 20 operably couple to the gears/couplers in a distal end of the main body portion (not shown) of the electromechanical instrument 10, such that a rotation of each drive shaft 66 rotates a correspondingly coupled driven member of the surgical instrument 10 to effectuate a discrete function of the surgical instrument (e.g., opening/closing of the end effector, articulation of the end effector, etc.)

The drive shafts 66 each have a drive gear 64 such as, for example, a spur gear, rotationally fixed thereabout. Each of the drive gears 64 are positioned at a discrete vertical location on their respective drive shaft 66, such that the drive gears 64 are vertically offset a selected distance from one another. Since the drive gears 64, in addition to being vertically offset, are also circumferentially spaced from one another, the drive gears 64 are offset from one another in all three dimensions. As mentioned above, the drive gears 64 each interface or intermesh with the gear teeth 68 on the inner periphery 70 of a corresponding ring gear 62 and receive torque therefrom originating from the respective motor 22.

In operation, the electromechanical instrument 10 is coupled to the instrument drive unit 20 by passing the main body portion of the electromechanical instrument 10 through the sleeve 28 of the instrument drive unit 20 in a proximal direction. The latch members 31a, 31b may engage opposing lateral sides of the main body portion of the surgical instrument 10 (FIG. 1) to selectively retain the surgical instrument 10 within the sleeve 28. With the main body portion of the electromechanical instrument 10 attached to the sleeve 28 of the instrument drive unit 28, the distal end portion 67b of each of the drive shafts 66 interfaces with corresponding gears/couplers (not shown) in the proximal end of the main body portion of the electromechanical instrument 10.

To actuate a particular function of the surgical instrument 10, such as, for example, an opening or closing of an end effector of the surgical instrument 10, one of the drive motors 22 of the instrument drive unit 20, such as the first drive motor 22a, is activated via the control device 4 (FIG. 1). An activation of the first drive motor 22a rotates the first motor shaft 40a. Rotation of the first motor shaft 40a actuates the first transmission assembly 60a to transfer torque from the first motor shaft 40a to a first driven member of the electromechanical instrument 10.

Figure 7:
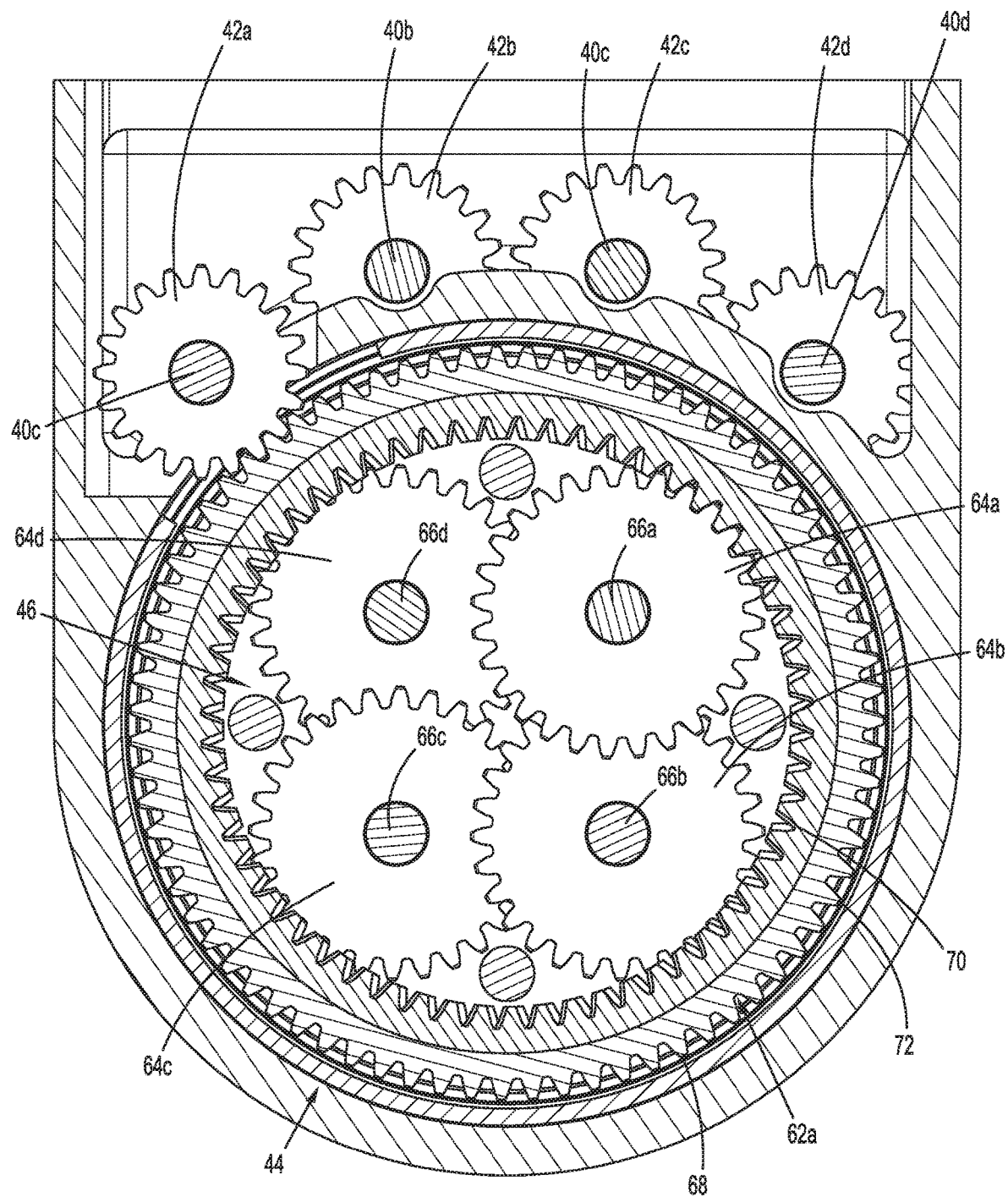
FIG. 7 is a side cross-sectional view of the instrument drive unit of FIG. 2.

In particular, with reference to FIG. 7, the first motor gear 42a of the first transmission assembly 60a rotates with the first motor shaft 40a, which, in turn, rotates the first ring gear 62a and the first drive gear 64a of the first transmission assembly 60a. Since the first drive gear 64a is rotationally fixed about the first drive shaft 66a, and the distal end portion 67b (FIG. 5) of the first drive shaft 66a is operably coupled to the proximal end of the first driven member of the surgical instrument 10 (FIG. 1), a rotation of the first drive gear 64a causes the first drive shaft 66a to rotate, thereby rotating the first driven member of the electromechanical instrument 10 to actuate an associated function of the surgical instrument 10. The drive motor 22e may be configured to resist rotation of the motor shaft 40e thereof during actuation of any of the transmission assemblies 60a, 60b, 60c, 60d so that actuation of one of the transmission assemblies 60a, 60b, 60c, 60d does not inadvertently result in a rotation of the hub 46.

To rotate the electromechanical instrument 10 about its longitudinal axis, the fifth drive motor 22e of the instrument drive unit 20 is activated by the control device 4 (FIG. 1). As noted above, an activation of the fifth drive motor 22e rotates the hub 46 about the central longitudinal axis "X." Due to the drive shafts 66 extending through the distal radial extension 58b of the hub 46 and the annular members 29 (FIG. 5) of the sleeve 28, the sleeve 28 rotates with the hub 46. Given that the electromechanical instrument 10 is non-rotationally supported in the sleeve 28, the electromechanical instrument 10 rotates with the sleeve 28 relative to the carriage 26 to change a rotational orientation of the electromechanical instrument 10. The drive motors 22a, 22b, 22c, 22d may be configured to concurrently rotate the motor shafts 40a, 40b, 40c, 40d, and in turn the drive gears 64a, 64b, 64c, 64d, with the hub 46 rotation. This would prevent rotation of the drive shafts 66a, 66b, 66c, 66d about their respective longitudinal axes during rotation of the hub 46, which may otherwise occur if the drive gears 64a, 64b, 64c, 64d were held stationary during rotation of the hub 46.

As can be appreciated, the instrument drive unit 20 described above improves usability of the surgical robotic system 1, reduces a foot-print of the overall system 1, improves safety architecture, reduces the time required to remove surgical instruments in case of an emergency, and simplifies the electronics used in the instrument drive unit 20.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use in a robotic surgical system, the instrument drive unit comprising:
   a carriage configured to be coupled to a robotic arm;
   a hub rotationally coupled to the carriage and configured to be non-rotatably coupled to an electromechanical surgical instrument;
   a plurality of motors;
   a plurality of motor gears, each motor gear of the plurality of motor gears operably coupled to a corresponding motor of the plurality of motors;
   a plurality of drive shafts rotationally supported in the hub, the plurality of drive shafts configured for interfacing with a corresponding driven member of the electromechanical surgical instrument;
   a plurality of drive gears, each drive gear of the plurality of drive gears fixed to a corresponding drive shaft of the plurality of drive shafts, wherein each motor gear of the plurality of motor gears is configured to rotate a corresponding drive gear of the plurality of drive gears in response to an activation of a respective motor of the plurality of motors to actuate a function of the electromechanical surgical instrument; and
   a plurality of ring gears, each ring gear of the plurality of ring gears operably coupling a corresponding motor gear of the plurality of motor gears with a corresponding drive gear of the plurality of drive gears, wherein at least a first ring gear of the plurality of ring gears has gear teeth on an inner periphery thereof and an outer periphery thereof, wherein the gear teeth on the inner periphery of the first ring gear interface with a corresponding drive gear of the plurality of drive gears, and the gear teeth on the outer periphery of the first ring gear interface with a corresponding motor gear of the plurality of motor gears.

2. The instrument drive unit according to claim 1, further comprising a drive motor operably coupled to the hub and configured to rotate the hub about a central longitudinal axis defined by the hub.

3. The instrument drive unit according to claim 2, wherein the drive motor has a rotatable coupling fixed to the hub to transfer torque from the drive motor to the hub.

4. The instrument drive unit according to claim 2, wherein the plurality of motors are circumferentially spaced from one another and disposed about the hub and the drive motor.

5. The instrument drive unit according to claim 1, further comprising a sleeve rotatably coupled to a distal end portion of the carriage and non-rotatably coupled to the hub, wherein the sleeve is configured to non-rotatably receive the electromechanical surgical instrument, such that a rotation of the hub results in a rotation of the electromechanical surgical instrument.

6. The instrument drive unit according to claim 1, wherein the plurality of ring gears are stacked within the hub.

7. The instrument drive unit according to claim 1, wherein a first ring gear of the plurality of ring gears and a first drive gear of the plurality of drive gears are operably coupled to one another and aligned along a first plane, and wherein a second ring gear of the plurality of ring gears and a second drive gear of the plurality of drive gears are operably coupled to one another and aligned along a second plane, stacked displaced from the first horizontal plane.

8. The instrument drive unit according to claim 1, wherein the plurality of ring gears are independently rotatable relative to one another.

9. The instrument drive unit according to claim 1, wherein the plurality of drive shafts are circumferentially spaced from one another about the hub.

10. The instrument drive unit according to claim 1, wherein the plurality of drive gears are offset from one another.

11. The instrument drive unit according to claim 1, wherein the plurality of motor gears are offset from one another.

12. The instrument drive unit according to claim 1, further comprising a plurality of motor shafts, each motor shaft of the plurality of motor shafts extending distally from a corresponding motor of the plurality of motors, each motor gear of the plurality of motor gears being fixed to a corresponding motor shaft of the plurality of motor shafts.

13. The instrument drive unit according to claim 1, wherein each drive shaft of the plurality of drive shafts has a distal end portion configured for interfacing with a corresponding driven member of the electromechanical surgical instrument.

14. An instrument drive unit for use in a robotic surgical system, the instrument drive unit comprising:
   a carriage configured to be coupled to a robotic arm;
   a plurality of motors supported in the carriage;
   a plurality of motor shafts, each motor shaft of the plurality of motor shafts extending distally from a corresponding motor of the plurality of motors, each motor shaft of the plurality of motor shafts having a motor gear fixed thereabout;
   a plurality of drive shafts circumferentially spaced from one another and configured for interfacing with a corresponding driven member of an electromechanical surgical instrument, each drive shaft of the plurality of drive shafts having a drive gear fixed thereabout, each drive gear being disposed at a discrete offset location relative to one another, wherein each motor gear is configured to rotate a corresponding drive gear in response to an activation of a respective motor of the plurality of motors to actuate a function of the electromechanical surgical instrument; and
   a plurality of stacked ring gears, each ring gear of the plurality of ring gears operably coupling a corresponding motor gear with a corresponding drive gear, such that each motor gear is configured to rotate a corresponding drive gear in response to an activation of a respective motor of the plurality of motors to actuate a function of the electromechanical surgical instrument, wherein at least a first ring gear of the plurality of ring gears has gear teeth on an inner periphery thereof and an outer periphery thereof, wherein the gear teeth on the inner periphery of the first ring gear interface with a corresponding drive gear of the plurality of drive gears, and the gear teeth on the outer periphery of the first ring gear interface with a corresponding motor gear of the plurality of motor gears.

15. The instrument drive unit according to claim 14, wherein a first ring gear of the plurality of ring gears and a first drive gear attached to a first drive shaft of the plurality of drive shafts are operably coupled to one another and aligned along a first plane, and wherein a second ring gear of the plurality of ring gears and a second drive gear attached to a second drive shaft of the plurality of drive shafts are operably coupled to one another and aligned along a second plane, displaced from the first plane.

16. The instrument drive unit according to claim 14, further comprising:
 a hub rotationally coupled to the carriage and configured to be non-rotatably coupled to the electromechanical surgical instrument, the plurality of drive shafts being rotationally supported in the hub; and
 a drive motor operably coupled to the hub and configured to rotate the hub about a central longitudinal axis defined by the hub.

17. The instrument drive unit according to claim 16, further comprising a sleeve rotatably coupled to a distal end portion of the carriage and non-rotatably coupled to the hub, wherein the sleeve is configured to non-rotatably receive the electromechanical surgical instrument, such that a rotation of the hub results in a rotation of the electromechanical surgical instrument.

18. An instrument drive unit for use in a robotic surgical system, the instrument drive unit comprising:
 a plurality of motors;
 a plurality of motor gears, each motor gear of the plurality of motor gears operably coupled to a corresponding motor of the plurality of motors;
 a plurality of drive shafts configured for interfacing with a corresponding driven member of an electromechanical surgical instrument;
 a plurality of drive gears, each drive gear of the plurality of drive gears fixed to a corresponding drive shaft of the plurality of drive shafts, wherein each motor gear of the plurality of motor gears is configured to rotate a corresponding drive gear of the plurality of drive gears in response to an activation of a respective motor of the plurality of motors to actuate a function of the electromechanical surgical instrument; and
 a plurality of ring gears, each ring gear of the plurality of ring gears operably coupling a corresponding motor gear of the plurality of motor gears with a corresponding drive gear of the plurality of drive gears, wherein at least a first ring gear of the plurality of ring gears has gear teeth on an inner periphery thereof and an outer periphery thereof, wherein the gear teeth on the inner periphery of the first ring gear interface with a corresponding drive gear of the plurality of drive gears, and the gear teeth on the outer periphery of the first ring gear interface with a corresponding motor gear of the plurality of motor gears, wherein the plurality of ring gears are stacked, wherein:
 a first ring gear of the plurality of ring gears and a first drive gear of the plurality of drive gears are operably coupled to one another and aligned along a first plane; and
 a second ring gear of the plurality of ring gears and a second drive gear of the plurality of drive gears are operably coupled to one another and aligned along a second plane, displaced from the first plane.

* * * * *